(12) United States Patent
Cheng et al.

(10) Patent No.: US 10,876,945 B2
(45) Date of Patent: Dec. 29, 2020

(54) METHOD FOR EVALUATING BREAKAGE STRENGTH OF FIRST AND SECOND CEMENTED SURFACES OF WELL CEMENTATION UNDER DYNAMIC LOAD

(71) Applicants: SouthWest Petroleum University, Chengdu (CN); China Academy of Building Research, Beijing (CN); CNPC Engineering Technology R&D Company Limited, Beijing (CN)

(72) Inventors: Xiaowei Cheng, Chengdu (CN); Dan Qin, Chengdu (CN); Kaiyuan Mei, Chengdu (CN); Kaiqiang Liu, Chengdu (CN); Gaoyin Zhang, Chengdu (CN); Xianshu Gao, Chengdu (CN); Jianzhou Jin, Chengdu (CN); Zhaijun Wen, Chengdu (CN); Yongjin Yu, Chengdu (CN); Chunmei Zhang, Chengdu (CN); Zaoyuan Li, Chengdu (CN); Xingguo Zhang, Chengdu (CN); Xiaoyang Guo, Chengdu (CN)

(73) Assignees: SOUTHWEST PETROLEUM UNIVERSITY, Chengdu (CN); CHINA ACADEMY OF BUILDING RESEARCH, Beijing (CN); CNPC ENGINEERING TECHNOLOGY R&D COMPANY LIMITED, Beijing (CN)

( * ) Notice: Subject to any disclaimer, the term of this patent is extended or adjusted under 35 U.S.C. 154(b) by 0 days.

(21) Appl. No.: 16/495,390

(22) PCT Filed: Jul. 13, 2018

(86) PCT No.: PCT/CN2018/095585
§ 371 (c)(1),
(2) Date: Sep. 19, 2019

(87) PCT Pub. No.: WO2019/140874
PCT Pub. Date: Jul. 25, 2019

(65) Prior Publication Data
US 2020/0011777 A1 Jan. 9, 2020

(30) Foreign Application Priority Data

Jan. 18, 2018 (CN) .......................... 2018 1 0050896

(51) Int. Cl.
*G01N 3/34* (2006.01)
*G01N 33/38* (2006.01)

(52) U.S. Cl.
CPC ............. *G01N 3/34* (2013.01); *G01N 33/383* (2013.01); *G01N 2203/0067* (2013.01); *G01N 2203/0075* (2013.01)

(58) Field of Classification Search
CPC .......... G01N 33/383; G01N 3/08; G01N 3/34; G01N 2203/0067; G01N 2203/0075; G01V 1/50; E21B 33/14
(Continued)

(56) References Cited

U.S. PATENT DOCUMENTS

| | | | |
|---|---|---|---|
| 6,266,994 B1 * | 7/2001 | Albertini | G01H 1/04 73/12.01 |
| 9,228,993 B2 * | 1/2016 | Shine, Jr. | G01N 33/383 |
| 2010/0212892 A1 | 8/2010 | Santra et al. | |

FOREIGN PATENT DOCUMENTS

| CN | 202560206 U | 11/2012 |
|---|---|---|
| CN | 102979505 A | 3/2013 |

(Continued)

*Primary Examiner* — Octavia Hollington
(74) *Attorney, Agent, or Firm* — Bayramoglu Law Offices LLC

(57) ABSTRACT

A method for evaluating the breakage strength of first and second cemented surfaces of well cementation under a dynamic load, includes: producing a rock-set cement-casing composite structure sample; clamping the sample between an incident rod and an output rod of a Hopkinson rod, hitting the incident rod with a conical punch to generate incident waves, enabling the incident waves to pass through the (Continued)

sample to generate reflected waves and projected waves, recording dynamic strain signals of incident waves, reflected waves and projected waves, and converting the dynamic strain signals into electrical signals and transmitting the electrical signals to a computer; recording the process and the corresponding time point from breakage starting to a complete breakage of the first and second cemented surfaces by a photographic instrument; obtaining a strain rate time travel curve and a stress-strain curve, and obtaining the corresponding breakage strength by analyzing the curve peak points.

3 Claims, 1 Drawing Sheet

(58) Field of Classification Search
USPC .......................................................... 73/789
See application file for complete search history.

(56) References Cited

FOREIGN PATENT DOCUMENTS

| | | |
|---|---|---|
| CN | 103184866 A | 7/2013 |
| CN | 105134170 A | 12/2015 |
| CN | 105422080 A | 3/2016 |
| CN | 105484729 A | 4/2016 |
| CN | 106959270 A | 7/2017 |

* cited by examiner

METHOD FOR EVALUATING BREAKAGE STRENGTH OF FIRST AND SECOND CEMENTED SURFACES OF WELL CEMENTATION UNDER DYNAMIC LOAD

CROSS REFERENCE TO THE RELATED APPLICATIONS

This application is the national phase entry of International Application No. PCT/CN2018/095585, filed on Jul. 13, 2018, which claims priority from Chinese Patent Application 201810050896.2, filed on Jan. 18, 2018, the entire contents of which are incorporated herein by reference.

TECHNICAL FIELD

The present invention relates to the field of well cementation of oil-gas wells, and more particularly provides a method for evaluating the breakage strength of first and second cemented surfaces of well cementation. By means of this method, the breakage process of the first and second cemented surfaces of a cement sheath caused by the impact of the dynamic load in the perforation and subsequent operations can be simulated, and meanwhile the simultaneous breakage strength of the first and second cemented surfaces under the dynamic load can be evaluated.

BACKGROUND

Cementing engineering is an important part of drilling operations and is the key to ensure subsequent normal proceeding of downhole operations.

For oil-gas wells, the most common breakage phenomenon is the breakage of a cemented interface. The cemented surface is divided into a first interface and a second interface. An interface formed by set cement and a casing serves as the first interface, and an interface formed by the set cement and a formation serves as the second interface. For composite materials, the cementation strength of the interfaces is generally weak; meanwhile, the set cement will shrink during the hardening process. The shrinkage of the set cement will reduce the cementation ability between the set cement and the formation, and is prone to cause the breakage to the second interface. The strong impact of post-production stimulation measures such as perforation and subsequent large-scale operations will cause the breakage to the first and second cemented surfaces (i.e., the first and second interfaces) of the cement sheath, and the breakage of the cemented surfaces will lead to oil and gas turbulence, reduced production, and even the scrapping of oil wells.

At present, more and more complex wells and special wells appear, so it is particularly important to test the cementation breakage strength of first and second interfaces of well cementation. Although domestic and foreign scholars have conducted some researches on the interface cementation performances, there is no suitable method to test the breakage strength of the cemented surfaces, and there is no uniform standard for breakage strength testing of the cemented surfaces. Therefore, it is necessary to carry out the testing of cementation breakage strength at the first and second interfaces of well cementation.

In recent years, domestic and foreign scholars have studied a lot of testing methods for the strength of first and second cemented surfaces, most of which are approximate simulation devices, such that the cementation strength is calculated in a case of ignoring other external force impact loads. All the cementation strength testing methods are used to measure the compressive strength by using the conventional "extrusion method", and then calculate the cementation strength by using formulas. The interface cementation strength error obtained by such methods is relatively large, and the actual downhole working conditions cannot be simulated.

There are several problems in the strength testing methods for the first and second cemented surfaces:

firstly, only is the testing of a single interface of a cemented surface considered. For example, "a Curing Device, Testing Device and Testing Method for Cementation Strength of an First Interface of Well Cementation" (CN2017102159656) is characterized in that cement slurry is poured into a curing drum, and only a first interface where set cement is in contact with the bottom of the drum can be obtained after the cement slurry is solidified; another example is "a Cementation Strength Testing Device for Second Interfaces of Well-Cementing Cement Sheath for Hydrated, Ice Formation" (CN2016100079968), which is also only able to test the cementation strength of a second interface, rather than simultaneously measuring the cementation strength of first and second interfaces.

Secondly, although some devices consider the first and second cemented surfaces at the same time, they do not consider the complicated downhole working conditions. The study on the cementation strength of the first and second interfaces of the cement sheath are mainly focused on single-axis static loading, and the cementation strength of the interface is obtained indirectly through the shear force, which is different from the impact breakage caused by subsequent operations. For example, an instrument used in "a Cementation Strength Testing Device for Well Cementation Cement" (CN2015110017554) is a common press, and a load generated by this press is also a static load.

Thirdly, although the load and the first and second interfaces are taken into account, the testing cannot be carried out in batches, and the dynamic load simulation testing process is too complicated and the operation is not convenient. For example, Tang Kai et al., in a logging company of Chuanqing Drilling Engineering Co., Ltd., has developed a perforation simulation device. Although this perforation simulation device can simulate perforation operations, it is not conducive to single-person testing, accompanied with a great breakage to a mold. Dynamic experimental equipment such as a hammer and an impact gun cannot achieve constant loading, accompanied with complicated equipment and high operating cost.

These research methods all attempt to simulate the true stress state of the cement sheath under the downhole working conditions, but based on the limitations of the experimental equipment and conditions, the cement sheath and the casing are rarely considered to be subjected to dynamic impact loads caused by subsequent stimulation operations such as perforation, acid fracturing and the like under the well. The breakages of the cementation strength of the first and second interfaces of the cement sheath have not been quantitatively evaluated.

SUMMARY

The present invention provides the following technical solution.

A plurality of rock-set cement-casing composite structure samples may be produced at once simultaneously by a simple device, which is conductive to testing and comparing breakage strengths for cemented surfaces. A sample production mold consists of an upper cover, a lower cover, a detachable middle mold body (a left part and a right part), as well as built-in round steel blocks and rock. A testing device is a Hopkinson rod tester working platform.

The method for evaluating the breakage strength of first and second cemented surfaces of well cementation under a dynamic load sequentially comprises the following steps:

(1) producing a rock-set cement-casing composite structure sample;

connecting the left part and the right part of the middle mold body with screws; fixing the lower cover to form a cuboid curing mold with a plurality of cylindrical inner cavities; placing steel blocks (simulating a casing) at the bottom of each of the inner cavities of the mold and then pouring cement slurry; placing round rock (simulating a well wall) on the surface, and covering with the upper cover which is provided with a groove for discharging redundant cement slurry; then placing the mold in a water bath kettle and curing to a desired age; demolding, and taking the round steel blocks, set cement and round rock out together to obtain the rock-set cement-casing composite structure sample;

(2) placing the sample on the Hopkinson rod testing platform for dynamic loading testing, to obtain the breakage strength of the first and second cemented surfaces through data processing analysis according to the following processes:

1) coating two end surfaces of the rock-set cement-casing composite structure sample with butter, and clamping the sample horizontally between an incident rod and an output rod of a Hopkinson rod;

2) hitting the incident rod with a conical punch to generate incident waves, enabling the incident waves to pass through the sample to generate reflected waves and projected waves, recording dynamic strain signals of the incident waves, the reflected waves and the projected waves by a strain gauge, and converting the dynamic strain signals into electrical signals and transmitting the electrical signals to a computer;

3) recording the process and the corresponding time point from breakage starting to a final complete breakage of the first and second cemented surfaces by taking photos with a high-speed photographic instrument in the loading process;

4) obtaining a strain rate time travel curve and a stress-strain curve by the computer, and obtaining the corresponding breakage strength by analyzing the curve peak points, wherein the corresponding point of the ordinate peak on the stress-strain curve is the simultaneous breakage strength of the first and second cemented surfaces under the dynamic load.

In the present invention, the curing mold steel is grade-N80 steel.

The contact surfaces of the round steel blocks and the cement slurry are sequentially washed with drilling fluid, rinsing liquid and isolation liquid for 3-5 minutes in advance to simulate the actual working conditions of the first cemented surface to which the drilling fluid is attached.

The contact surfaces of the circular rock and the cement slurry are pressure-filtered with an API high temperature and high pressure press filter to form a filter cake on the end surface of the round rock to simulate the adhesion of the filter cake on the second cemented surface.

Compared with the prior art, the present invention has the following beneficial effects:

(1) An objective of the present invention is to provide a method for evaluating the breakage strength of first and second cemented surfaces of well cementation under a dynamic load. Dynamic loading of an impact is performed at two ends of a rock-set stone-casing composite structure by using a Hopkinson rod, which can truly simulate the impact of the formation perforation and subsequent operations such as acid fracturing on the cement sheath and the casing. Meanwhile, drilling fluid is attached to the first interface of the cement sheath, and the filter cake is attached to a second interface to simulate the downhole working conditions more truly.

(2) under the condition of comprehensive consideration of the actual production conditions and experimental measurement conditions, the design and processing are performed according to the actual specification and dimension proportions, to obtain an equivalent sample model of the first and second interfaces under more actual working conditions;

(3) in the rock-set stone-casing composite structure, the influence factors among a plurality of downhole structures, the influence of the filter cake and the drilling fluid system, and the coupling effect of the filter cake and the drilling fluid system acting on two interfaces at the same time are fully considered;

(4) different from the current static evaluation method for cemented surface strength, the Hopkinson rod is used to test the dynamic breakage strength of the first and second cemented surfaces, and the dynamic impact breakage is closer to a breakage mode under actual working conditions;

(5) this evaluation method can simultaneously evaluate the breakage strength that can be borne by the first and second cemented surfaces under a dynamic load, and can well observe the breakage of the first and second interfaces after being impacted, and obtain data of the two interfaces at the same time through once evaluation, so as to avoid the effects of uncertainty caused by separation analysis.

In drawings, reference symbols represent the following components: 1-round rock; 2-second interface; 3-set cement; 4-first interface; 5-round steel block.

Figure 3:
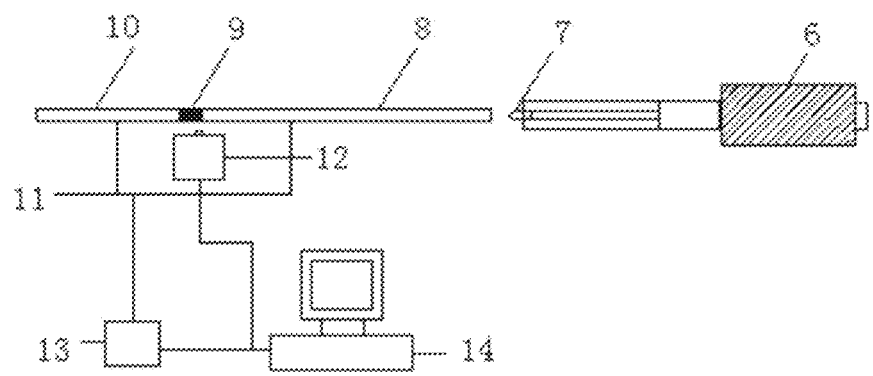

FIG. 3 is a structural diagram of a device for performing dynamic loading testing when the sample is placed on a Hopkinson rod testing platform.

In drawings, reference symbols represent the following components: 6-launching device; 7-conical punch; 8-incident rod; 9-sample; 10-output rod; 11-strain foil; 12-high-speed photographic instrument; 13-strain gauge; 14-computer.

DETAILED DESCRIPTION

The present invention will now be further described below with reference to the accompanying drawings and embodiments.

Figure 1:
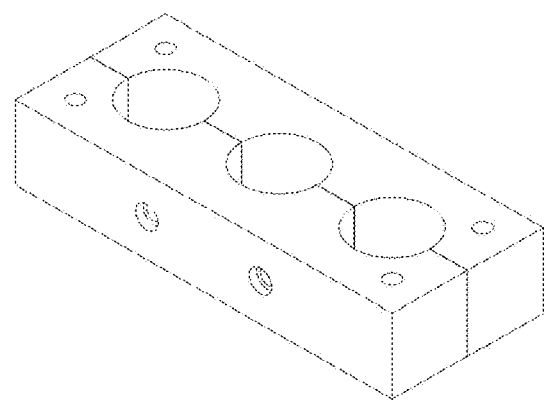
FIG. 1 is a structural schematic diagram of a curing mold of the present invention.

Referring to FIG. 1, the curing mold is a cuboid having a plurality of cylindrical inner cavities.

Figure 2:
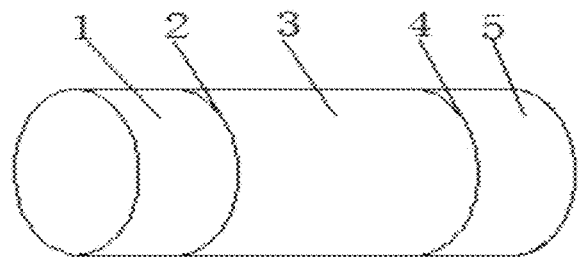
FIG. 2 is a schematic diagram of a rock-set cement-casing composite structure sample of the present invention.

Referring to FIG. 2, circular rock 1 simulates a well wall, circular steel blocks 5 simulate the casing, an interface between the circular rock 1 and set cement 3 serves as a second interface 2, and an interface between the set cement 3 and the circular steel blocks 5 serves as a first interface 4.

The structure of a device for dynamic loading testing when the sample is placed on a Hopkinson rod testing platform is shown in FIG. 3. A conical punch 7 of a launching device 6 hits an incident rod 8, and a sample 9 is horizontally clamped between the incident rod 8 and an output rod 10. A high-speed photographic instrument 12 is placed directly in front of the sample, and a strain foil is attached to the incident rod 8 and the output rod 10. A strain gauge 13 is connected between the strain foil 11 and the high-speed photographic instrument 12, and the strain gauge 13 and the high-speed photographic instrument 12 are connected to a computer 14 respectively.

The method for evaluating the breakage strength of first and second cemented surfaces of well cementation under a dynamic load comprises the following steps:

1. production of a sample (1) coating the contact surfaces of a curing mold and the cement slurry with a proper amount of mold-releasing oil, and discharging water for sealing testing before pouring;

(2) placing the round steel blocks at the bottom of each of the inner cavities of the mold, and sequentially washing the contact surfaces of the round steel blocks and the cement slurry with drilling fluid, rinsing liquid and isolation liquid for 3-5 minutes in advance to simulate the actual working conditions of the first cemented surface to which the drilling fluid is attached;

(3) pouring the prepared cement slurry to the round inner cavities of the curing mold, placing the round rock that simulates a formation on the surface, and pressure-filtering the contact surfaces of the circular rock and the cement slurry with an API high temperature and high pressure press filter to form a filter cake, simulating the adhesion of the filter cake on the second interface, and finally covering with the upper cover of the curing mold, tightening a nut, wiping off the cement slurry overflowing the surface, and placing the mold into a water bath kettle for curing;

(4) taking the curing mold out, and dismantling the upper cover, the lower cover, the left middle mold body and the right middle mold body to obtain the complete rock-set cement-casing composite structure sample.

2. Evaluation Method (1) coating two end surfaces of the rock-set cement-casing sample with butter, placing the sample between the incident rod and the output rod of the Hopkinson rod for an experiment, and performing horizontal impacting by using a constant air pressure, such that the conical punch placed in a launching cavity impacts the incident rod, and constant strain rate loading can be achieved by using the generated half sinusoidal stress waves (horizontal impacting can be performed by the impact load in large operations such as simulation perforations at different constant pressures). The strain rate of a perforating gun ranges from 2000 to 5000 $s^{-1}$, and the strain rate of the Hopkinson impact test (SHPB) (see Table 1 for specific simulation parameters) can meet the requirements of this range;

TABLE 1

Simulation Parameters for Dynamic Loading Testing

| Simulating dimensions of formation and casing | Bullet velocity | Air pressure | Simulating downhole load |
|---|---|---|---|
| The formation has an inner diameter of 10 mm, the casing has an outer diameter of 10 mm and the cement sheath has a thickness of 30 mm | Less than 40 m/s | 0.2-5.8 MPa | SHPB dynamic load (strain rate $10^1$-$10^3$) |

(2) The strain gauge and the high-speed photographic instrument are turned on at the time of impact loading. When the conical punch hits the incident rod to generate incident waves, and the incident waves pass through the sample to generate reflected waves and projected waves. These three waves are sensed by the strain foil attached to the incident rod and the output rod and converted into electrical signals by the strain gauge and recorded by the computer;

(3) the breakage process of the sample under a dynamic load, that is, the process from breakage starting to the final complete breakage of the first and second cemented surfaces under dynamic load impacting, is recorded with the high-speed photographic instrument;

(4) the collected data is processed and analyzed with computer data processing software to obtain a strain rate time travel curve and a stress-strain curve. The corresponding point of the ordinate peak on the stress-strain curve is the simultaneous breakage strength of the cemented surfaces under the dynamic load.

The present invention can simulate the dynamic impact load generated by the large-scale operations such as perforation completion and later acidizing fracturing on the casing and the cement sheath, and test the dynamic breakage strength that can be borne by the first and second cemented surfaces of the rock-set cement-casing composite structure under the dynamic load. Through dynamic loading, the experimental results are closer to the actual conditions.

The above content refers only to the embodiments of the present invention. It should be noted that those skilled in the art can make improvements without departing from the principles of the present invention, and such improvements are within the protection scope of the claims of the present invention.

What is claimed is:

1. A method for evaluating a breakage strength of first and second cemented surfaces of a well cementation under a dynamic load, sequentially comprising the following steps:

(1) producing a rock-set cement-casing composite structure sample;

connecting a left part and a right part of a middle mold body with screws; fixing a lower cover to form a cuboid curing mold with a plurality of cylindrical inner cavities; placing round steel blocks at a bottom of each of the plurality of cylindrical inner cavities and then pouring a cement slurry; placing a round rock on a surface of the cement slurry, and covering with an upper cover, the upper cover is provided with a groove for discharging a redundant cement slurry; then placing the mold in a water bath kettle and curing to a desired age;

demolding, and taking the round steel blocks, set cement and the round rock out together to obtain the rock-set cement-casing composite structure sample;

(2) placing the rock-set cement-casing composite structure sample on a Hopkinson rod testing platform for a dynamic load loading testing, to obtain the breakage strength of the first and second cemented surfaces through a data processing analysis according to the following sub-steps:

sub-step 1) coating two end surfaces of the rock-set cement-casing composite structure sample with butter, and clamping the rock-set cement-casing composite structure sample horizontally between an incident rod and an output rod of a Hopkinson rod;

sub-step 2) hitting the incident rod with a conical punch to generate incident waves, the incident waves pass through the rock-set cement-casing composite structure sample to generate reflected waves and projected waves, recording dynamic strain signals of the incident waves, the reflected waves and the projected waves by a strain gauge, and converting the dynamic strain signals into electrical signals and transmitting the electrical signals to a computer;

sub-step 3) recording a process and a corresponding time point from breakage starting to a final complete breakage of the first and second cemented surfaces by taking photos with a high-speed photographic instrument in the loading process;

sub-step 4) obtaining a strain rate time travel curve and a stress-strain curve by the computer, and obtaining the breakage strength by analyzing curve peak points, wherein a corresponding point of an ordinate peak on the stress-strain curve is a simultaneous breakage strength of the first and second cemented surfaces under the dynamic load.

2. The method for evaluating the breakage strength of the first and second cemented surfaces of well cementation under the dynamic load according to claim 1, wherein contact surfaces of the round steel blocks and the cement slurry are sequentially washed with a drilling fluid, a rinsing liquid and an isolation liquid for 3-5 minutes in advance to simulate the actual working conditions of the first cemented surface to which the drilling fluid is attached.

3. The method for evaluating the breakage strength of the first and second cemented surfaces of the well cementation under the dynamic load according to claim 1, wherein contact surfaces of the round rock and the cement slurry are pressure-filtered with a high temperature and high pressure press filter to form a filter cake to simulate adhesion of the filter cake on the second cemented surface.

* * * * *